United States Patent [19]
Zhao et al.

[11] Patent Number: 6,048,316
[45] Date of Patent: Apr. 11, 2000

[54] MEDICAL DIAGNOSTIC ULTRASONIC IMAGING SYSTEM AND METHOD FOR DISPLAYING COMPOSITE FUNDAMENTAL AND HARMONIC IMAGES

[75] Inventors: Danhua Zhao, Milpitas; Patrick Phillips, Sunnyvale, both of Calif.

[73] Assignee: Acuson Corporation, Mountain View, Calif.

[21] Appl. No.: 09/174,063

[22] Filed: Oct. 16, 1998

[51] Int. Cl.⁷ .................................................. A61B 8/00
[52] U.S. Cl. .................................................. 600/447
[58] Field of Search .................................. 600/440–441, 600/443, 447, 454–456, 458; 367/7, 138

[56] References Cited

U.S. PATENT DOCUMENTS

| | | |
|---|---|---|
| Re. 34,566 | 3/1994 | Ledley . |
| Re. 35,148 | 1/1996 | Lizzi et al. . |
| 3,617,994 | 11/1971 | Glenn et al. . |
| 3,640,271 | 2/1972 | Horton . |
| 3,771,116 | 11/1973 | Farrah . |
| 4,290,310 | 9/1981 | Anderson . |
| 4,322,974 | 4/1982 | Abele et al. . |
| 4,445,379 | 5/1984 | Yamaguchi et al. . |
| 4,475,397 | 10/1984 | Riley et al. . |
| 4,534,221 | 8/1985 | Fife et al. . |
| 4,662,222 | 5/1987 | Johnson . |
| 4,694,699 | 9/1987 | Cheeke . |
| 4,712,037 | 12/1987 | Verbeek et al. . |
| 4,783,839 | 11/1988 | Bamber . |
| 4,803,994 | 2/1989 | Burke . |
| 4,872,346 | 10/1989 | Kelly-Fry et al. . |
| 4,913,157 | 4/1990 | Pratt, Jr. et al. . |
| 5,111,823 | 5/1992 | Cohen . |
| 5,111,824 | 5/1992 | Lazenby et al. . |
| 5,115,809 | 5/1992 | Saitoh et al. . |
| 5,135,000 | 8/1992 | Akselrod et al. . |
| 5,158,071 | 10/1992 | Umemura et al. . |
| 5,187,687 | 2/1993 | Burckhardt et al. . |
| 5,195,520 | 3/1993 | Schlief et al. . |
| 5,197,477 | 3/1993 | Peterson et al. . |

(List continued on next page.)

FOREIGN PATENT DOCUMENTS

| | | |
|---|---|---|
| 0357164 B1 | 10/1991 | European Pat. Off. . |
| 0770352 A1 | 5/1997 | European Pat. Off. . |
| 0851241 A2 | 7/1998 | European Pat. Off. . |
| 890072 | 12/1981 | Russian Federation . |
| WO 98/20361 | 5/1998 | WIPO . |

OTHER PUBLICATIONS

U.S. application No. 60/032,771, Powers et al., filed Nov. 26, 1996.

"Abstract Session IV Contrast and Ischemia" and "Poster Session A New Technologies". (May 1995) *Journal of the American Society of Echocardiography*, vol. 8, No. 3.

(List continued on next page.)

*Primary Examiner*—Francis J. Jaworski
*Attorney, Agent, or Firm*—Brinks Hofer Gilson & Lione

[57] ABSTRACT

An ultrasonic imaging system and method acquire fundamental mode and harmonic mode ultrasonic image signals with a transducer from a subject under examination. These image signals are then combined to form a composite image. This composite image includes two lateral edgefield image regions modulated primarily as a function of the fundamental mode ultrasonic image signals, and a centerfield image region modulated primarily as a function of the harmonic mode image signals. In this way, improved image quality can be obtained throughout the imaged field of view.

28 Claims, 3 Drawing Sheets

U.S. PATENT DOCUMENTS

| | | |
|---|---|---|
| 5,233,994 | 8/1993 | Shmulewitz . |
| 5,255,683 | 10/1993 | Monaghan . |
| 5,259,384 | 11/1993 | Kaufman et al. . |
| 5,287,753 | 2/1994 | Routh et al. . |
| 5,313,948 | 5/1994 | Murashita et al. . |
| 5,357,964 | 10/1994 | Spivey et al. . |
| 5,358,466 | 10/1994 | Aida et al. . |
| 5,379,642 | 1/1995 | Reckwerdt et al. . |
| 5,379,770 | 1/1995 | Van Veen . |
| 5,386,830 | 2/1995 | Powers et al. . |
| 5,396,285 | 3/1995 | Hedberg et al. . |
| 5,409,688 | 4/1995 | Quay . |
| 5,410,205 | 4/1995 | Gururaja . |
| 5,410,516 | 4/1995 | Uhlendorf et al. . |
| 5,417,213 | 5/1995 | Prince . |
| 5,417,214 | 5/1995 | Roberts et al. . |
| 5,425,366 | 6/1995 | Reinhardt et al. . |
| 5,433,204 | 7/1995 | Olson . |
| 5,433,207 | 7/1995 | Pretlow, III . |
| 5,435,311 | 7/1995 | Umemura et al. . |
| 5,438,554 | 8/1995 | Seyed-Bolorforosh et al. . |
| 5,443,071 | 8/1995 | Banjanin et al. . |
| 5,456,255 | 10/1995 | Abe et al. . |
| 5,456,257 | 10/1995 | Johnson et al. . |
| 5,462,057 | 10/1995 | Hunt et al. . |
| 5,469,849 | 11/1995 | Sasaki et al. . |
| 5,471,990 | 12/1995 | Thirsk . |
| 5,479,926 | 1/1996 | Ustuner et al. . |
| 5,482,046 | 1/1996 | Deitrich . |
| 5,526,816 | 6/1996 | Arditi . |
| 5,540,909 | 7/1996 | Schutt . |
| 5,558,092 | 9/1996 | Unger et al. . |
| 5,560,364 | 10/1996 | Porter . |
| 5,568,813 | 10/1996 | Deitrich et al. . |
| 5,577,505 | 11/1996 | Brock-Fisher et al. . |
| 5,579,768 | 12/1996 | Klesenski . |
| 5,579,770 | 12/1996 | Finger . |
| 5,588,435 | 12/1996 | Weng et al. . |
| 5,600,675 | 2/1997 | Engeler . |
| 5,601,085 | 2/1997 | Ostensen et al. . |
| 5,601,086 | 2/1997 | Pretlow, III et al. . |
| 5,608,690 | 3/1997 | Hossack et al. . |
| 5,617,862 | 4/1997 | Cole et al. . |
| 5,628,322 | 5/1997 | Mine . |
| 5,632,277 | 5/1997 | Chapman et al. . |
| 5,667,373 | 9/1997 | Wright et al. . |
| 5,713,356 | 2/1998 | Kruger . |
| 5,720,289 | 2/1998 | Wright et al. . |
| 5,724,976 | 3/1998 | Mine et al. . |
| 5,740,128 | 4/1998 | Hossack et al. . |
| 5,779,640 | 7/1998 | Holley et al. ............................ 600/447 |
| 5,873,829 | 2/1999 | Kamiyama et al. ..................... 600/443 |
| 5,897,500 | 4/1999 | Zhao ....................................... 600/443 |
| 5,908,389 | 6/1999 | Roundhill et al. ....................... 600/443 |
| 5,967,985 | 10/1999 | Hayakawa ............................... 600/447 |
| 5,993,392 | 11/1999 | Roundhill et al. ....................... 600/447 |

OTHER PUBLICATIONS

"HP Ultrasound Technologies—Viability." (1997) *About HP Ultrasound Imaging*, WWW document.

"Supplement to Journal of the American College of Cardiology" (Mar. 24–27, 1996) American College of Cardiology, 45$^{th}$ Annual Scientific Session, pp. 21A, 63A, 239–240A.

Abbott, JG et al. (1979) "Acoustic Speckle: Theory and Experimental Analysis", *Ultrason. Imaging*, vol. 1, pp. 303–374.

Abbott, JG. (1978) "Multi–Scan Processing In A Phased Array Imaging System", *Ultrasonics Symposium Proceedings*, IEEE Cat. #78CH 1344—ISU.

Amir, et al. (Jul. 1986) "Analysis and Comparison of some frequency compounding algorithms for the reduction of ultrasonic clutter" *IEEE*, vol. UFFC–33, No. 4, pp. 402–411.

Anson, LW et al. (Apr. 1993) "Ultrasonic scattering from spherical shells including viscous and thermal effects." *J. Acoustical Society of America*, vol. 93, No. 4.

Armstrong, W et al. (Jun. 6, 1994) "American Society of Echocardiography Position Paper on Contrast Echocardiography." draft 1.

Averkiou, MA et al. (Nov. 1993) "Self–demodulation of amplitude–and frequency–modulated pulses in a thermoviscous fluid." *J. Acoustical Society of America*, vol. 94. No. 5.

Chang, PH et al. (Nov. 1996) "Second Harmonic Imaging and Harmonic Doppler Measurements with Albunex." *IEEE Transactions on Ultrasonics, Ferroelectrics, and Frequency Control*, vol. 42, No. 6.

Chen, EJ et al., (Jan. 1996) "Young's Modulus Measurements of Soft Tissues with Application to Elasticity Imaging." IEEE Transactions on Ultrasonics, Ferroelectrics, and Frequency Control, vol. 43, No. 1.

Christopher, T. (Jan. 1997) "Finite Amplitude Distortion––Based Inhomogeneous Pulse Echo Ultrasonic Imaging." *IEEE Transactions on Ultrasonics, Ferroelectrics, and Frequency Control*, vol. 44, No. 1, pp. 125–139.

de Jong, N. "Physical properties and technical aspects of ultrasound contrast agents." (one page).

Elbaum, M et al. (Jun. 1972) "A Wavelength Diversity Technique For Reduction Of Speckle Size", *Optics Communications*, vol. 5, No. 3.

Elbaum, M et al., (1976) "SNR in photocounting images of rough objects in partially coherent light", *Applied Optics*, vol. 2268.

Entrekin, R et al., (Sep. 1979) "Real Time Speckle Reduction In B–Mode Images", *IEEE Ultrasonics Symposium Proceedings*.

Gensane, M. (Jun. 1994) "Bubble population measurements with a parametric array." *1994 Acoustical Society of America*, vol. 95, No. 6.

Gottlieb, S et al. (1995) "Effect of Pressure on Echocardiographic Videodensity from Sonicated Albumin: An In Vitro Model." *J. Ultrasound Med.* vol. 14.

Hossack, JA et al. (Mar. 1993) "Improving the Characteristics of a Transducer Using Multiple Piezoelectric Layers." *IEEE Transactions on Ultrasonics, Ferroelectrics, and Frequency Control*, vol. 40, No. 2.

Hossack, JA et al. (19920"Improving transducer performance using multiple active layers." SPIE vol. 1733.

Ishihara, K et al. (1988) "New Approach to Noninvasive Manometry Based on Pressure Dependent Resonant Shift of Elastic Microcapsules in Ultrasonic Frequency Characteristics." Japanese J. of Applied Physics, vol. 2.

Jones–Oliveira, JB et al. (Aug. 1994) "Transient fluid—solid interaction of submerged spherical shells revisited: Proliferation of frequencies and acoustic radiation effects." Acoustical Society of America, 96(2) Pt. 1.

Karrer, HE et al. (1980) "A Phased Array Acoustic Imaging System for Medical Use." 1980 Ultrasonics Symposium.

Kino, GS. (1979) Acoustic Imaging for Nondestructive Evaluation, *Proceedings of the IEEE*, vol. 67, No. 4.

Lee, Jr., F et al. (1991) "Sonoelasticity Imaging: Results in in Vitro Tissue Specimens." Radiology, vol. 181, No. 1.

Lee, YS et al. (Feb. 1985) "Time–domain modeling of pulsed finite–amplitude sound beams." 1995 Acoustical Society of America, 97 (2).

Leighton, TG. "Transient excitation of insonated bubbles." *Research Notes*.

Lerner, RM et al. (1990) "Sonoelasticity Images Derived from Ultrasound Signals in Mechanically Vibrated Tissues." *Ultrasound Med. & Biol.*, vol. 16, No. 3.

Longuet–Higgins, MS. (1991) Resonance in nonlinear bubble oscillations. *J. Fluid Mech.* vol. 224.

Magnin PA et al., (1982) "Frequency Compounding for Speckle Contrast Reduction in Phased Array Images" *Ultrasonic Imaging*, vol. 4, No. 3, pp. 267–281.

Mei, CC et al. (1991) "Parametric resonance of a spherical bubble." *J. Fluid Mech.* vol. 229.

Newhouse, VL et al. (May 1984) "Bubble size measurements using the nonlinear mixing of two frequencies." *J. Acoust. Soc. Am.* vol. 75, No. 5.

Norris, JW. (1994) "The non–linear oscillation of a radially symmetric bubble in a time periodic pressure field." *Dynamics and Stability of Systems*, vol. 9, No. 1.

Ophir, J. et al. (1991) "Elastography: A Quantitative Method for Imaging the Elasticity of Biological Tissues." *Ultrasonics Imaging* vol. 13.

Parker, DL et al., (1982) "Analysis of B–Scan Speckle Reduction by Resolution Limited Filtering", *Ultrasonic Imaging* vol. 4, pp. 108–125.

Parker, KJ et al. (1992) "Sonoelasticity of Organs: Shear Waves Ring a Bell." *J. Ultrasound Med.*, vol. 11.

Parker, KJ et al. (1990) "Tissue Response to Mechanical Vibrations for 'Sonoelasticity Imaging'." *Ultrasound in Med. & Biol.*, vol. 16, No. 3.

Rubens, DJ et al. (1995) "Sonoelasticity Imaging of Prostate Cancer: In Vitro Results." *Radiology*, vol. 995, No. 2.

Sato, K et al. (May 1994) "Numerical analysis of a gas bubble near a rigid boundary in an oscillatory pressure field." *J. Acoustical Society of America*, vol. 95, No. 5.

Schrope, B et al. (1992) "Simulated Capillary Blood Flow Measurement Using A Nonlinear Ultrasonic Contrast Agent," *Ultrasonic Imaging* vol. 14.

Sehgal, CM et al. (1995) "Influence of Postprocessing Curves on Contrast—Echographic Imaging: Preliminary Studies." *J. Ultrasound Med*, vol. 14.

Sehgal, CM et al. (1995) "Sonographic Enhancement of Renal Cortex by Contrast Media." *J. Ultrasound Med.* vol. 14.

Uhlendorf, V et al. (1994) "Nonlinear Acoustical Response of Coated Microbubbles in Diagnostic Ultrasound." *1994 Ultrasonics Symposium*.

MEDICAL DIAGNOSTIC ULTRASONIC IMAGING SYSTEM AND METHOD FOR DISPLAYING COMPOSITE FUNDAMENTAL AND HARMONIC IMAGES

BACKGROUND

This invention relates to ultrasonic imaging systems and methods, and particularly to ultrasonic imaging systems and methods that utilize both harmonic and fundamental imaging modes.

Ultrasonic imaging systems that combine ultrasonic images from multiple transmit beams to form a single improved image are described for example in U.S. Pat. Nos. 5,568,813; 5,111,824; 5,462,057; and 5,579,770. The methods described in these patents however do not address the issue of providing high image quality in harmonic images of technically difficult examinations.

Hossack et al. U.S. patent application Ser. No. 08/904,825, assigned to the assignee of the present invention, discloses a method and system that combine nearfield harmonic imaging and farfield fundamental imaging to create a single improved image. This application also discloses a system and method that combine a nearfield image which is an amplitude matched combination of fundamental and harmonic signals with a farfield fundamental image to form a single improved image.

Danhua Zhao U.S. Pat. No. 5,897,500, assigned to the assignee of the present invention, discloses a method and system that combines nearfield fundamental imaging and middlefield or farfield imaging to create a single composite image. In one system and method, nearfield and farfield regions are modulated primarily as a function of fundamental mode image signals and a middlefield region is modulated primarily as a function of harmonic mode image signals.

In spite of the improvements provided in the above identified Hossack and Danhua Zhao applications, a need presently exists for an ultrasonic imaging system and method that provide improved lateral imaging, particularly for use in harmonic imaging systems used to image tissue without added contrast agent. In such cases, particularly in technically difficult examinations, the lateral performance may be less than optimum because of degradation of image signals along edge lines. For example, the signal to noise ratio decreases along edge lines for vector and sector scan formats.

SUMMARY

The present invention is defined by the following claims, and nothing in this section should be taken as a limitation on those claims. By way of introduction, it can be stated that the method and apparatus described below acquire fundamental mode ultrasonic image signals and harmonic mode ultrasonic image signals from a subject. The fundamental and harmonic mode image signals are combined to form a composite image, which includes rightfield and leftfield image regions that are modulated primarily as a function of the fundamental mode ultrasonic image signals, and a centerfield image region that is modulated primarily as a function of the harmonic mode ultrasonic image signals. By using the fundamental mode image signals preferentially in the rightfield and leftfield, image quality is enhanced while the detail resolution and improved reduction in image clutter artifact associated with harmonic imaging is maintained.

DETAILED DESCRIPTION OF THE PRESENTLY PREFERRED EMBODIMENT

Figure 1:
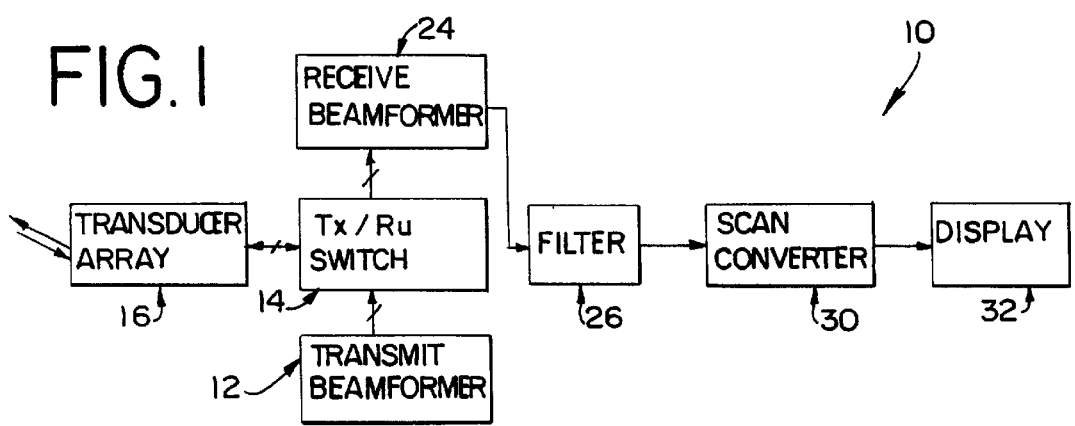
FIG. 1 is a block diagram of an ultrasonic imaging system that incorporates a presently preferred embodiment of this invention.

Turning now to the drawings, FIG. 1 shows a block diagram of a medical ultrasonic imaging system 10 that provides improved image quality by combining leftfield fundamental, centerfield harmonic, and rightfield fundamental images together to create a composite image providing improved signal to noise ratio and consistent enhanced detail resolution in the lateral dimension.

The system 10 includes a transmit beamformer 12, a transmit/receive switch 14, a phased transducer array 16, a receive beamformer 24, a filter 26, a scan converter 30, and a display 32. The transmit beamformer 12 generates shaped transmit waveforms so that the transmitted harmonic frequency power is suppressed. Unshaped waveforms may also be used. The receive beamformer 24 is operative to form an acoustic beam at either the received fundamental frequency, or at a harmonic of the received fundamental frequency, such as the second harmonic for example. The filter 26 is adjustable to pass either the fundamental signals or the harmonic signals, such as a bandpass filter or a demodulator and low pass filter. By passing either fundamental or harmonic signals, the system 10 operates in a fundamental or a harmonic mode. The scan converter 30 is operative to store at least two received acoustic beams and to splice them into a single scan line as described below.

Figure 2:
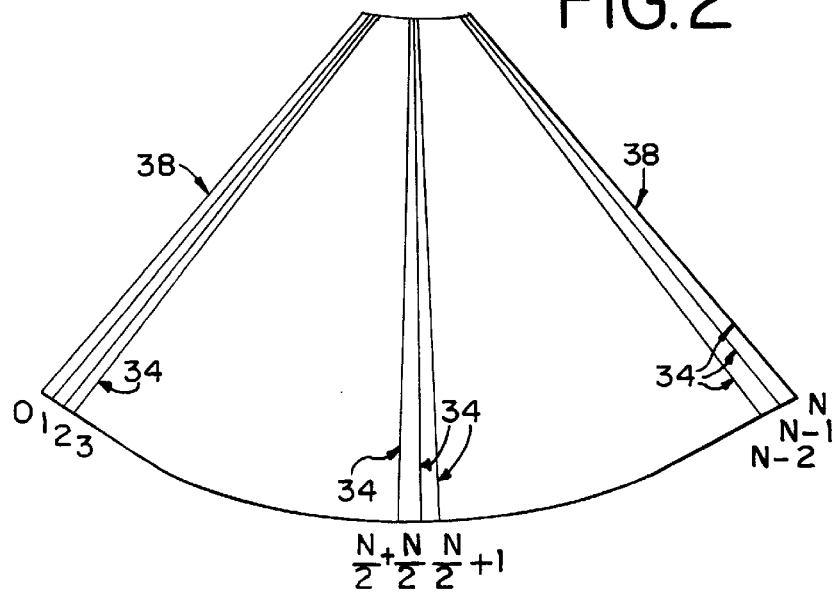
FIG. 2 is a schematic diagram of a vector scan pattern.

FIG. 2 is a schematic diagram of a vector scan pattern. Each transmitted waveform is focused along one of a plurality of N scan lines 34. The received acoustic beams are also focused along the scan lines 34. Multiple foci along any or all the scan lines 34 may be used. Information along each entire scan line 34 is obtained. An entire scan line comprises information along a range of depths used to generate an image.

The scan lines 34 are formatted to image an area or region 36 of a subject. As shown, the region 36 is imaged with a vector format where the scan lines 34 (1 through N) vary by different angles. The further towards a lateral edge 38, the greater the angle relative to a normal from the transducer array 16 (FIG. 1). Different angular relationships between various scan lines and between scan lines and the transducer array 16 (FIG. 1) may be used. In alternative embodiments, sector, curved vector, linear, curver linear or other formats are used.

Figure 3:
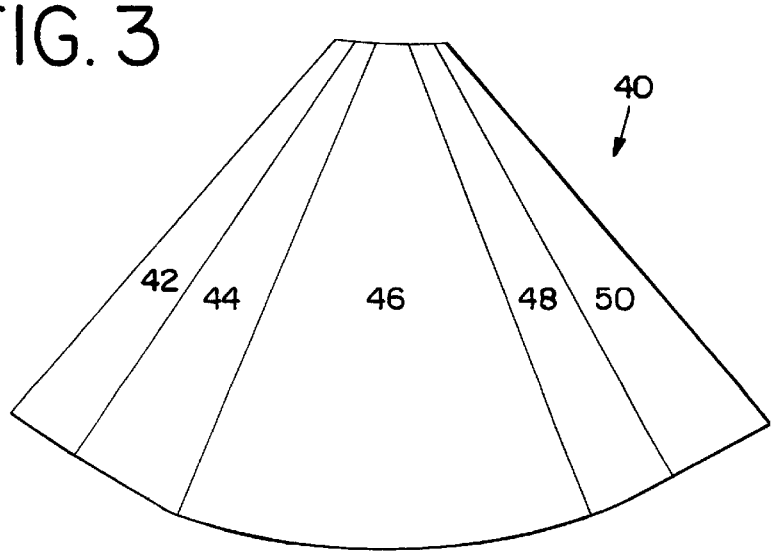
FIG. 3 is a schematic diagram of a composite image generated with the system of FIG. 1.

FIG. 3 is a schematic diagram of a composite image 40 formed on the display 32 of FIG. 1. The image 40 includes five separate regions: a leftfield region 42, a centerfield region 46, a rightfield region 50, a leftfield compounded region 44, and a rightfield compounded region 48. The terms leftfield, centerfield, and rightfield are not intended to define any specific scan lines or lateral dimensions. Rather, these terms define relative scan line positions or lateral dimensions, with the leftfield region 42 being further left on the image than the rightfield region 50. The rightfield region 42 and leftfield region 50 comprise edgefields that are adjacent a lateral edge or closer to a lateral edge of the image 40 than the centerfield region 46

Additional or different regions may be used with or without compounded regions. For example, a composite image associated with only two laterally divided regions, one modulated as a function of harmonic information and the other modulated as a function of fundamental information, may be generated.

The system 10 generates a series of fundamental beams for regions associated with fundamental information, such as the leftfield region 42, rightfield region 50, leftfield compounded region 44 and rightfield compounded region 48. The system 10 also generates a series of harmonic beams for regions associated with harmonic information, such as the centerfield region 46, leftfield compounded region 44 and rightfield compounded region 48. As discussed below, the rightfield and leftfield regions 42 and 50 may also include some harmonic information and the centerfield region 46 may also include some fundamental information.

Figure 4:
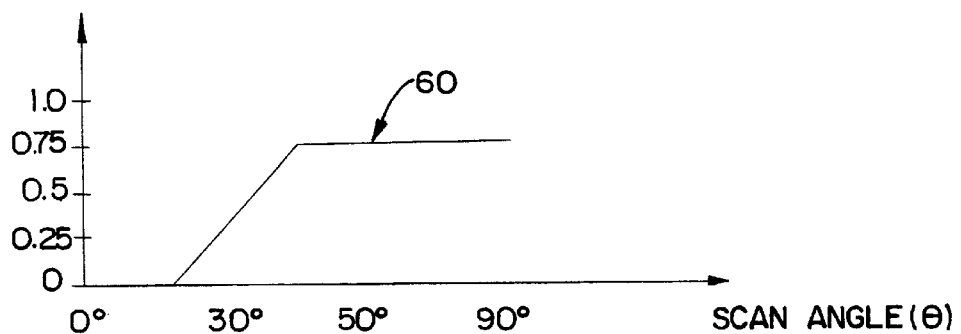
FIGS. 4 and 5 are graphs of fundamental and harmonic weighting functions, respectively, used in the formation of the image of FIG. 3.
Figure 5:
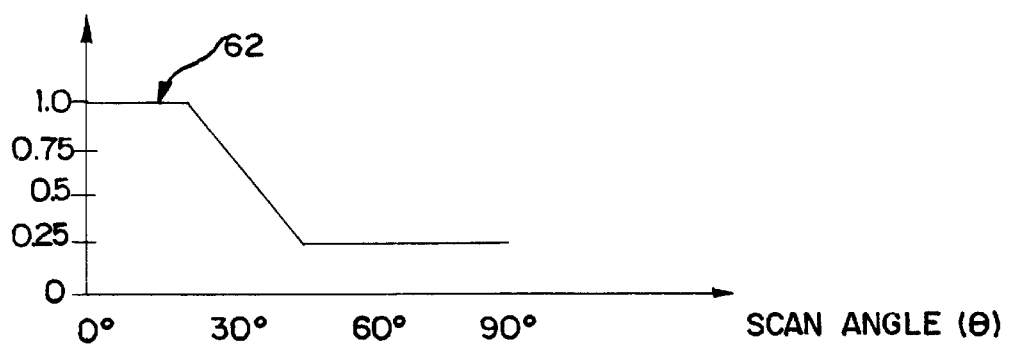

The system 10 combines harmonic and fundamental information associated with the same scan line 34. Two piece-wise linear weighting functions as shown in FIGS. 4 and 5 control the combination. The fundamental weighting function 60 of FIG. 4 has a magnitude of zero in the centerfield region 46, such as associated with scan line angles of 0 through 20 degrees. The function 60 increases linearly from 0 to 0.75 in the rightfield and leftfield compounded regions 44 and 48, such as associated with scan line angles of 21 through 35 degrees. The function 60 remains at 0.75 for the leftfield and rightfield regions 42 and 50, such as associated with scan lines angles greater than 35 degrees. Although the function 60 is shown as a linear function in the two compounded regions in FIG. 4, nonlinear functions can also be used. Furthermore, different angles may be used for the beginning and ending of the compounded regions 44 and 48, and different angles or functions may be used for the leftfield compounded region 44 than for the rightfield compounded region 48.

The harmonic weighting function 62 of FIG. 5 is formed by subtracting the function 60 from 1 and clipping the minimum to 0.25, such that the sum of the two weighting functions 60, 62 is equal to 1.0 for scan line angles of 0 through 45 degrees. In alternative embodiments, the harmonic weighting function 62 is not clipped, is clipped at a different angle or magnitude, or is not related to the fundamental weighting function 60 as a function of subtraction from 1.

In an alternative embodiment, the percentage or weight of the harmonic information varies linearly from 100% for a scan line angle of 0 degrees to 10% for a scan line angle of 45 degrees. The percentage or weight of the fundamental information varies linearly from 0% for a scan line angle of 0 degrees to 90% for a scan line angle of 45 degrees. Other angles and nonlinear relationships may be used. In this embodiment, the rightfield and leftfield regions 50 and 42 are associated with information modulated primarily as a function of fundamental information, such as a fundamental weight of 75% or more. Conversely, the centerfield region 46 is associated with information modulated primarily as a function of harmonic information, such as a harmonic weight of 75% or more. Other weights, larger or smaller than 75%, may be used.

The fundamental and harmonic beams are combined in the scan converter by multiplying the fundamental beam by the fundamental weighting function 60 of FIG. 4, multiplying the harmonic beam by the harmonic weighting function 62 of FIG. 5, and then summing the weighted fundamental and harmonic beams to create a composite beam that is used for display purposes.

Figure 6:
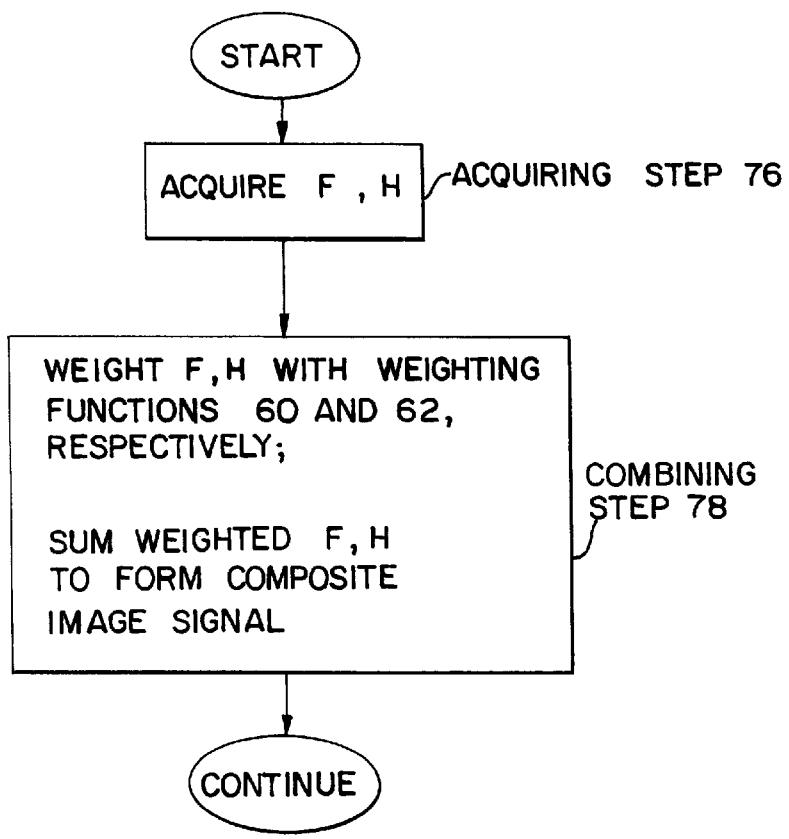
FIG. 6 is a block diagram of a method practiced by the system 10 of FIG. 1.

This method practiced by the system 10 in forming the composite image 40 is flow charted in FIG. 6. As shown in step 76, the first step in this method is to acquire the required image signals. In this case two separate image signals are acquired, each along the same lateral direction. The first image signal F is a fundamental mode image signal. The second image signal H is a harmonic mode image signal.

The next step 78 in the method of FIG. 6 is a combining step which includes two component parts. First, the two image signals F and H acquired in step 76 are weighted or multiplied by weighting functions 60 and 62, respectively, as shown in FIGS. 4 and 5. The final portion of the combining step 78 is to sum the weighted image signals F and H to form the composite image signal that is displayed. The method is then continued with the other sets of image signals as appropriate to obtain the composite image signals for the each position along the scan line 34 and for other scan lines 34.

The acquiring step 76 is performed by the elements 12 through 26 of FIG. 1, and the combining step 78 of FIG. 6 is performed by the scan converter 30 of FIG. 1.

Figure 7:
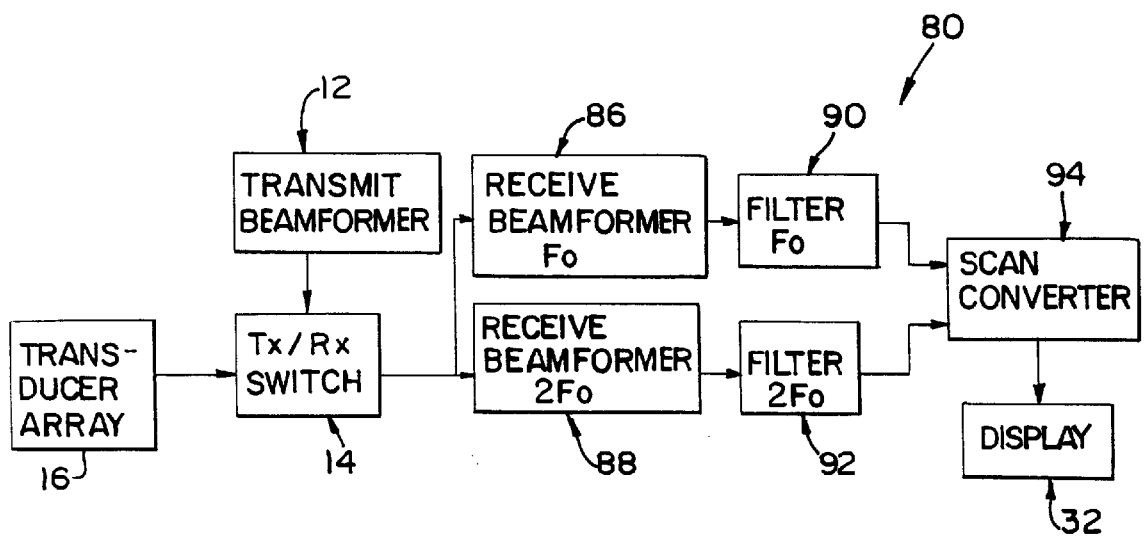
FIG. 7 is a block diagram of another ultrasonic imaging system that incorporates a preferred embodiment of this invention.

FIG. 7 is a block diagram of another ultrasonic imaging system 80 that can be used to practice alternative embodiments of this invention. The system 80 includes a transmit beamformer 12, a transmit/receive switch 14, and a transducer array 16 as described above.

The system 80 also includes two separate receive beamformers 86, 88 in parallel. The receive beamformer 86 forms a receive beam at the fundamental frequency $F_0$, while the receive beamformer 88 forms a receive beam at a second harmonic frequency $2F_0$. The fundamental and harmonic receive beams are applied to parallel filters 90, 92, respectively, before they are combined in the scan converter 94. The combined signal is then supplied for display on the display 32. Because both the fundamental and the receive beams are acquired from the same transmit event, the system 80 improves frame rates and reduces motion artifacts as compared to the system 10 of FIG. 1.

The embodiments described above provide the advantages of improved lateral edgefield imaging performance. This improvement in edgefield imaging performance results in an overall image quality that is improved and preserved throughout the lateral dimension.

In an alternate embodiment, the composite image 40 also includes the nearfield, farfield and/or middlefield regions discussed in U.S. applications, Ser. Nos. 08/993,947 and 08/638,918. The composite image 40 may include a center region modulated primarily as a function of harmonic image signals surrounded azimuthally and laterally by nearfield, farfield, leftfield and rightfield regions modulated primarily as a function of fundamental image signals. Compounded regions may also be included.

In other alternative embodiments, any of the regions are associated with information combined as a function of a plurality of types of information. For example, the centerfield region is responsive to a combination of information associated with second and third harmonics. Other frequency bands may be used.

Of course the present invention can be implemented in many other ways. The harmonic and fundamental mode image signals can be acquired using the widest variety of filtering and demodulation techniques. Transmit focal length can be varied as desired, and both single and multiple transmit focus techniques can be used. The multiple image signals combined to form the composite image signal can be obtained in parallel or sequentially. Various beamformers, filters and the like can be used, including those employing analog and digital signal processing techniques.

Similarly, the image signals can be combined to form the composite image signal using many techniques, including look up tables and analog or digital circuits for scaling and summing signals. The combining step can be performed at any desired point in image signal processing after beam formation, and the compounded regions discussed above are not required in all applications.

This invention can be used both with and without the addition of contrast agent to the region being imaged. When contrast agent is added, it can be of any suitable type, including a variety of microbubbles. Particular advantages are obtained when no contrast agent is added to the region of interest throughout the imaging session, which may correspond to a medical diagnostic examination. In this case, the harmonic signal return from the edgefield portion of the imaged region is particularly weak, and improved edgefield images are obtained by using the fundamental image signal for the edgefield region as discussed above.

As used herein, the terms fundamental and harmonic mode image signals are intended broadly. Fundamental mode image signals are formed primarily in response to ultrasonic echoes at the same ultrasonic frequency as the dominant transmitted ultrasonic frequency. Harmonic mode ultrasonic image signals are formed primarily in response to ultrasonic echoes having a frequency different from that of the dominant transmitted ultrasonic frequency. The term harmonic is intended broadly to encompass subharmonics, fractional harmonics, and integral harmonics of two or greater. Second harmonic image modes have been found to be particularly useful in clinical applications.

As pointed out above, the term lateral edgefield is intended to signify a portion of the imaged tissue left or right from the center or another portion of the image. The absolute ranges may vary broadly.

When an imaged region is said to be modulated primarily as a function of a fundamental or a harmonic image signal, the term primarily is intended broadly to include image regions that are modulated solely or mostly as a function of the respective harmonic or fundamental signals. When an imaged region is said to be modulated as a function of a fundamental or a harmonic image signal, the term modulation is intended broadly to include image regions that are responsive solely to the fundamental or harmonic signals, respectively, or one of the respective fundamental or harmonic signals and other signals, such as respective harmonic and fundamental signal. For example, an image region modulated as a function of a harmonic signal may also be responsive to fundamental information (e.g., 50% harmonic and 50% fundamental).

The foregoing detailed description has described only a few of the many forms that the present invention can take. For this reason, this detailed description is intended as an illustration of specific forms of the invention, and not as a definition of the invention. It is only the following claims, including all equivalents, that are intended to define the scope of this invention.

We claim:

1. An ultrasonic imaging method comprising the following steps:
   (a) acquiring fundamental mode ultrasonic image signals and harmonic mode ultrasonic image signals with a transducer;
   (b) combining the fundamental and harmonic mode image signals of step (a) to form a composite image, said composite image comprising a first image region that is modulated as a function of the fundamental mode ultrasonic image signals and a second image region that is modulated primarily as a function of the harmonic mode ultrasonic image signals, the first image region being along entire scan lines at a lateral edge portion of the composite image and the second image region being along entire scan lines at a center portion of the composite image.

2. The method of claim 1 wherein the composite image formed in step (b) further comprises a third, lateral edgefield region that is modulated as a function of the fundamental mode ultrasonic signals.

3. The method of claim 1 wherein the composite image formed in step (b) further comprises a compounded region intermediate the first and second image regions, said compounded region modulated as a function of both the fundamental mode image signals and the harmonic mode image signals, and said first region modulated primarily as a function of the fundamental mode ultrasonic image signals.

4. The method of claim 2 wherein the composite image formed in step (b) further comprises first and second compounded regions, said first compounded region intermediate the first and second image regions, said second compounded region intermediate the second and third image regions, said first and second compounded regions modulated as respective functions of both the fundamental mode image signals and the harmonic mode image signals, and said third region modulated primarily as a function of the fundamental mode image signals.

5. The method of claim 1 wherein step (a) comprises the step of acquiring the fundamental mode and harmonic mode ultrasonic image signals in a sector scan format.

6. The method of claim 1 wherein step (a) comprises the step of acquiring the fundamental mode and the harmonic mode ultrasonic image signals in a format selected from the group consisting of: linear, vector and curved vector.

7. The method of claim 1 wherein step (a) is performed during an ultrasonic medical diagnostic examination session, further comprising the step of (c) maintaining the subject free of added contrast agent throughout the examination session.

8. The method of claim 1 wherein step (a) comprises the step of acquiring at least some of the fundamental and the harmonic mode image signals in parallel.

9. A medical ultrasonic diagnostic imaging system adapted to provide a composite image comprising:
   a first image region modulated as a function of fundamental mode ultrasonic image signals acquired along entire scan lines at a lateral edgefield portion of the composite image;
   a second image region modulated primarily as a function of harmonic mode ultrasonic image signals acquired along entire scan lines at a centerfield portion of the composite image.

10. An ultrasonic imaging system comprising:
    means for acquiring fundamental mode ultrasonic image signals and harmonic mode ultrasonic image signals with a transducer;

means for combining the fundamental and harmonic mode image signals to form a composite image, said composite image comprising a first image region that is modulated as a function of the fundamental mode ultrasonic image signals and a second image region that is modulated primarily as a function of the harmonic mode ultrasonic image signals, the first image region being along entire scan lines at a lateral edge portion of the composite image and the second image region being along entire scan lines at a center portion of the composite image.

11. The invention of claims 9 or 10 wherein the composite image is associated with a scan format selected from the group consisting of: linear, sector, curved vector and vector.

12. The invention of claims 9 or 10 wherein the first and second image regions comprise centerfield and rightfield regions, respectively, of the composite image.

13. The invention of claims 9 or 10 wherein the first and second regions comprise centerfield and leftfield regions, respectively, of the composite image.

14. The invention of claim 13 wherein the composite image further comprises a third, rightfield region that is modulated as a function of the fundamental mode ultrasonic image signals.

15. The method of claim 14 wherein the composite image further comprises first and second compounded regions, said first compounded region intermediate the first and second image regions, said second compounded region intermediate the second and third image regions, said first and second compounded regions modulated as respective functions of both the fundamental mode image signals and the harmonic mode image signals, and said first and third regions modulated primarily as a function of the fundamental mode ultrasonic image signals.

16. The invention of claims 9 or 10 wherein the composite image further comprises a compounded region, intermediate the first and second image regions, said compounded region modulated as a function of both the fundamental mode image signals and the harmonic mode image signals, and the first image region modulated primarily as a function of the fundamental mode ultrasonic image signals.

17. The invention of claim 10 wherein the acquiring means comprises means for acquiring the fundamental and harmonic mode image signals sequentially.

18. The invention of claim 10 wherein the acquiring means comprises means for acquiring the fundamental and harmonic mode image signals in parallel.

19. The invention of claims 1, 9 or 10 wherein the first region is modulated substantially only as a function of the fundamental mode ultrasonic image signals, without any substantial contribution from the harmonic mode ultrasonic image signals.

20. The invention of claims 1, 9 or 10 wherein the second region is modulated substantially only as a function of the harmonic mode image signals, without any substantial contribution from the fundamental mode ultrasonic image signals.

21. The invention of claims 1, 9 or 10 wherein the fundamental and harmonic mode ultrasonic image signals contribute at least 75% and at most 25%, respectively, to the first region and the fundamental and harmonic mode ultrasonic image signals contribute at most 25% and at least 75%, respectively, to the second region.

22. An ultrasonic imaging method comprising the following steps:

(a) acquiring fundamental mode ultrasonic image signals and harmonic mode ultrasonic image signals with a transducer;

(b) combining the fundamental and harmonic mode image signals of step (a) to form a composite image, said composite image comprising a first image region that is modulated as a function of the fundamental mode ultrasonic image signals, a second image region that is modulated primarily as a function of the harmonic mode ultrasonic image signals, a compound image region that is modulated as a function of both the fundamental mode image signals and the harmonic mode image signals, the first image region being at a lateral edge portion of the composite image, the second image region being at a center portion of the composite image and the compound region being intermediate of the first and second image regions.

23. The method of claim 22 wherein the composite image formed in step (b) further comprises a third, lateral edgefield region that is modulated as a function of the fundamental mode ultrasonic image signals.

24. The method of claim 23 wherein the composite image formed in step (b) further comprises a second compound region that is modulated as a function of both the fundamental mode image signals and the harmonic mode image signals, said second compound region intermediate the second and third image regions, and said first and third regions modulated primarily as a function of the fundamental mode ultrasonic image signals.

25. The method of claim 22 wherein step (a) is performed during an ultrasonic medical diagnostic examination session, further comprising the step of (c) maintaining the subject free of added contrast agent throughout the examination session.

26. The method of claim 22 wherein the composite image formed in step (b) further comprises azimuthal nearfield and farfield regions that are each modulated as a function of one of fundamental and harmonic mode image signals.

27. A medical ultrasonic diagnostic imaging system adapted to provide a composite image comprising:

a first image region modulated as a function of fundamental mode ultrasonic image signals acquired at a lateral edgefield portion of the composite image;

a second image region modulated primarily as a function of harmonic mode ultrasonic image signals acquired at a centerfield portion of the composite image; and a compounded region, intermediate the first and second image regions, said compounded region modulated as a function of both the fundamental mode image signals and the harmonic mode image signals.

28. The method of claim 27 wherein the composite image further comprises:

a third image region modulated as a function of fundamental ultrasonic image signals at a second lateral edgefield portion of the composite image; and a second compounded regions, said second compounded region intermediate the second and third image regions, said second compounded regions modulated as respective functions of both the fundamental mode image signals and the harmonic mode image signals.

* * * * *